United States Patent [19]

Taenzer et al.

[11] Patent Number: 4,476,874

[45] Date of Patent: Oct. 16, 1984

[54] ULTRASONIC IMAGING WITH VOLUME FLOW MEASURING METHOD AND APPARATUS

[75] Inventors: Jon C. Taenzer, Palo Alto; Donald J. Burch, Los Altos; Philip S. Green, Atherton, all of Calif.

[73] Assignee: SRI International, Menlo Park, Calif.

[21] Appl. No.: 383,568

[22] Filed: Jun. 1, 1982

[51] Int. Cl.$^3$ .............................................. A61B 10/00
[52] U.S. Cl. .................................... 128/663; 128/660; 73/861.25
[58] Field of Search ........................ 128/660, 661, 663; 73/861.25

[56] References Cited

U.S. PATENT DOCUMENTS

| | | |
|---|---|---|
| 3,498,290 | 3/1970 | Shaw et al. |
| 3,896,788 | 7/1975 | Sato |
| 3,901,077 | 8/1975 | McCarty et al. |
| 3,977,247 | 8/1976 | Hassler |
| 4,067,236 | 1/1978 | Hottinger |
| 4,095,597 | 6/1978 | Hassler |
| 4,103,679 | 8/1978 | Aronson ............................ 128/663 |
| 4,141,347 | 2/1979 | Green et al. |
| 4,182,173 | 1/1980 | Papadofrangakis et al. |
| 4,227,407 | 10/1980 | Drost |
| 4,228,687 | 10/1980 | Fraser ............................ 128/663 X |
| 4,257,278 | 3/1981 | Papadofrangakis et al. |
| 4,370,985 | 2/1983 | Takeichi et al. ..................... 128/663 |
| 4,373,533 | 2/1983 | Iinuma .............................. 128/663 |

OTHER PUBLICATIONS

Brandestini, M. "Topoflow-A Digital Full Range Doppler Velocity Meter", IEEE Trans. on Sonics & UTS, vol. SU-25, No. 5, Sep. 1978.
Marich, K. N. et al., "An Improved Medical UTS Imaging System", UTS Imaging 3, No. 4, 309-322, Oct. 1981.
Nealeigh, R. et al., "A Venous Pulse Doppler Flowmeter", ISA Transactions, vol. 15, No. 1, pp. 84-87, 1976.
Chihara, K. "A UTS Multichannel Doppler Flowmeter", Conference EEMTIC '81, Electrical & Electronic Meas. Conf., Ottawa, Canada, Sep. 22-24, 1981.
"Human Carotid Artery Diameter and Flow by a Non-invasive Technique", Olson & Cooke, Med. Instr. V9#2, Mar.-Apr. 1975, pp. 99-101.
"A Non-Destructive Ultrasonic Technique to Measure Diameter and Blood Flow in Arteries", Olson and Cooke, IEEE Trans. on Biomed. Engr., vol. BME-21, No. 2, pp. 168-171, Mar. 1974.
"Pulsed Ultrasonic Doppler Blood-Flow Sensing", Baker, IEEE Trans. on Sonics & Ultrasonics, vol. SU-17, #3, Jul. 1970, pp. 170-185.
"Ultrasonic Duplex Echo-Doppler Scanner", Barber et al., IEEE Trans. on Biomed Engr., vol. BME-21, No. 2, Mar. 1974, pp. 109-113.

Primary Examiner—Kyle L. Howell
Assistant Examiner—Francis J. Jaworski
Attorney, Agent, or Firm—Victor R. Beckman

[57] ABSTRACT

Method and apparatus for obtaining quantitative velocity profile measurements and for displaying the same are disclosed. From such velocity measurements, instantaneous volume flow within a vessel across which the measurements are obtained is calculated. In one operating mode, a real-time display of quantitative velocity profiles is provided together with a scrolling display of a plurality of total instantaneous volume flow measurements. In another operating mode, velocity profiles obtained at corresponding points in successive cardiac cycles are averaged to obtain a plurality of average velocity profiles which are selectively displayed under operator control. In this mode of operation, a fixed display of total instantaneous volume flow measurements obtained over a period of time which includes at least one cardiac cycle is provided. A movable pointer adjacent the display of total instantaneous volume flow values and under operator control is provided to identify the point in the cardiac cycle selected for display of an associated velocity profile. Means for calculating volume flow over a cardiac cycle, and for numerically displaying said average also is provided. Depth control means control both depth and gain functions of the pulsed Doppler system.

22 Claims, 12 Drawing Figures

FIG-7A
FIG-7B
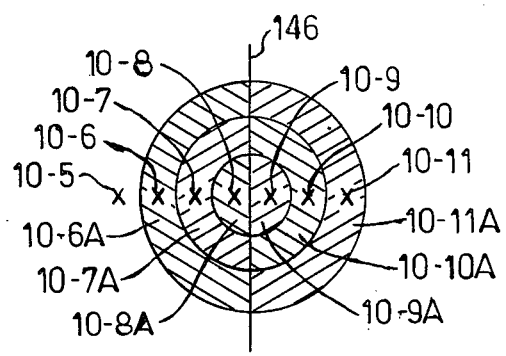
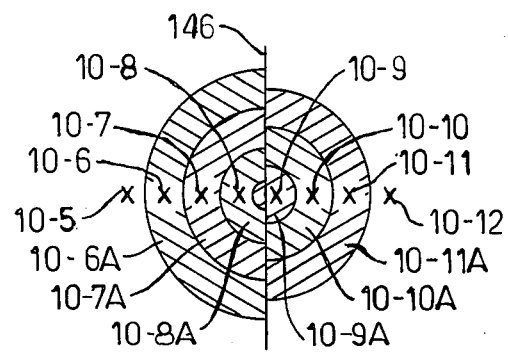
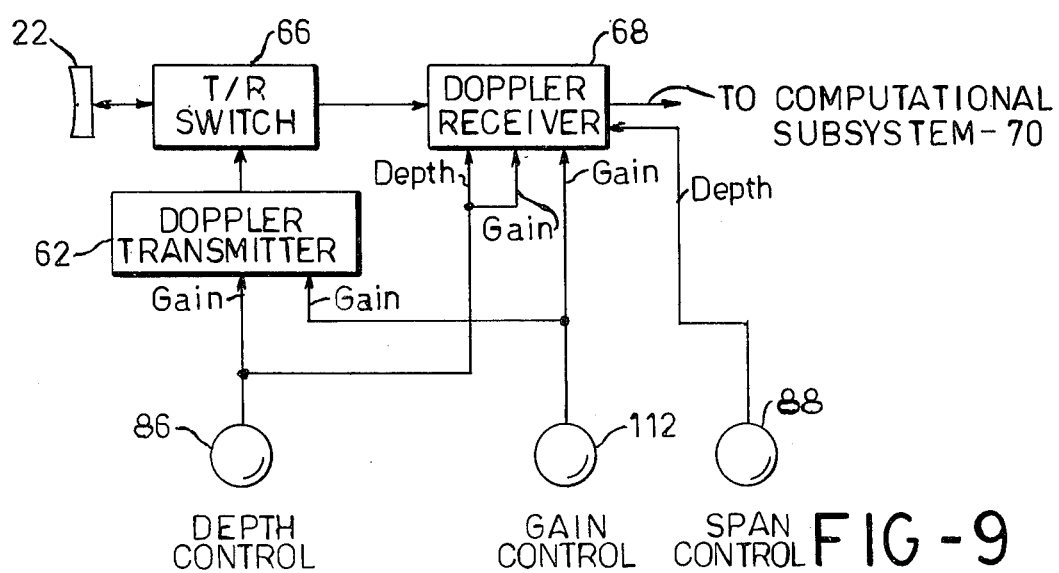
FIG-9

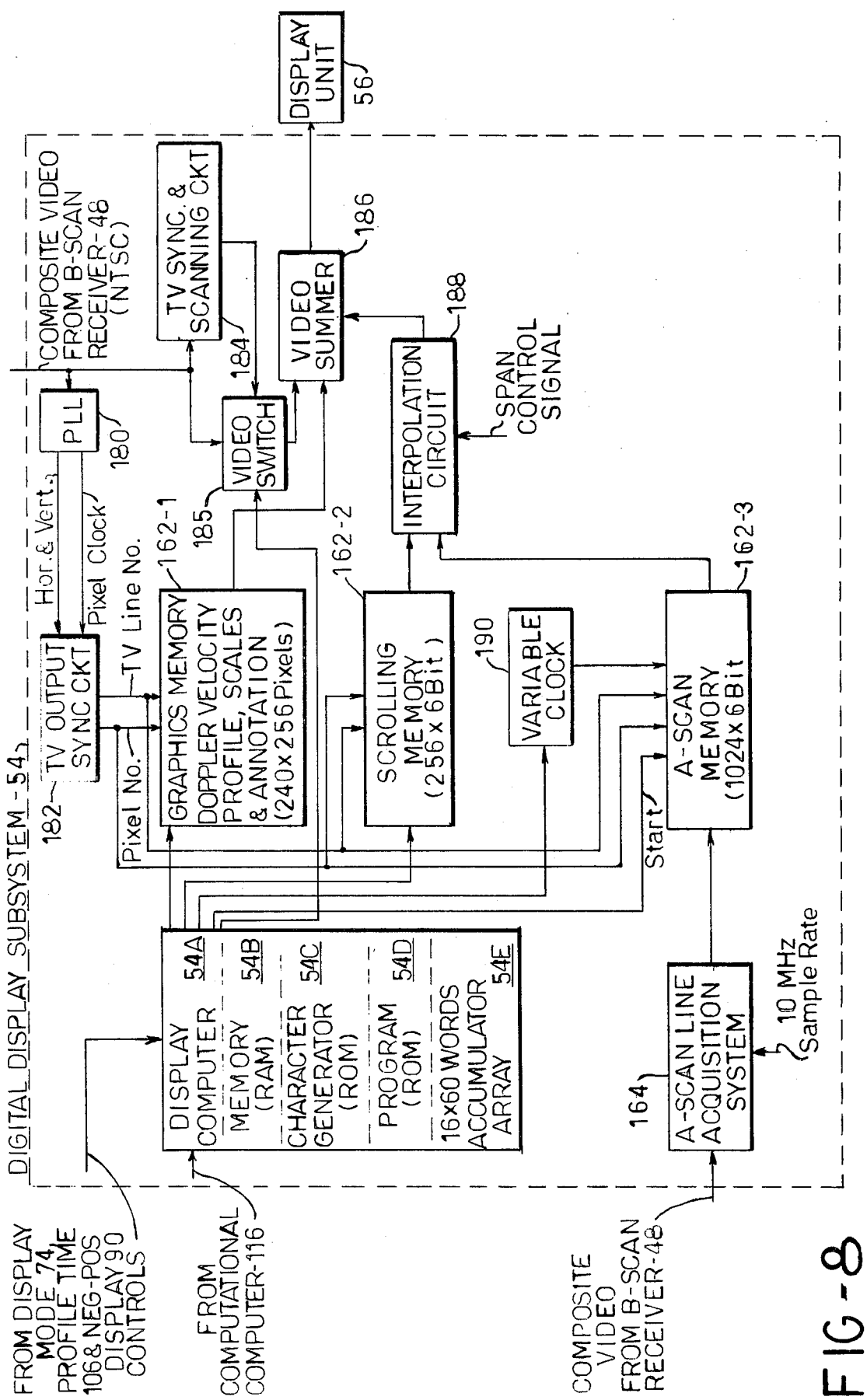

ULTRASONIC IMAGING WITH VOLUME FLOW MEASURING METHOD AND APPARATUS

BACKGROUND OF THE INVENTION

This invention relates to ultrasonic imaging and Doppler effect measuring method and apparatus for real-time imaging and quantitative measurement of volume flow in a vessel, such as a blood vessel.

Combinations of B-scan imaging and pulsed Doppler motion detecting means for use in the display of a B-scan image together with a blood flow velocity profile are well known as disclosed, for example, in U.S. Pat. No. 4,141,347 by Philip S. Green et al, issued Feb. 27, 1979, and in an article entitled "Ultrasonic Duplex Echo-Doppler Scanner", Barber et al, IEEE Transactions on Biomedical Engineering, Vol. BME-21, No. 2, March 1974, pp. 109–113. With these arrangements, only qualitative, not quantitive, real time blood volume flow measurements are possible. Quantitative measures of blood volume flow are highly desirable for assessment of vascular disease due to atherosclerosis or other causes.

Method and apparatus for the quantitative measurement of volumetric blood flow also are known as shown in the following U.S. Pat. Nos.: 3,498,290—Shaw et al; 3,896,788—Sato; 3,901,077—McCarty et al; 3,977,247—Hassler; 4,067,236—Hottinger; 4,095,597—Hassler; 4,103,679—Aronson; 4,182,173—Papadofrangakis et al; 4,227,407—Drost; and 4,257,278—Papadofrangakis et al. Publications showing quantitative measurement of volumetric blood flow include: "Human Carotid Artery Diameter and Flow by a Non-invasive Technique", Olson and Cooke, Med. Instr. V 9 #2, March-April 1975, pp. 99–101; "A Non-destructive Ultrasonic Technique to Measure Diameter and Blood Flow in Arteries", Olson and Cooke, IEEE Trans. on Biomed. Engr., Vol. BME-21, No. 2, March 1974, pp. 168–171; and "Pulsed Ultrasonic Doppler Blood-Flow Sensing", Baker, IEEE Trans. on Sonics and Ultrasonics, Vol. SU-17, #3, July 1970, pp. 170–184. Prior art volumetric blood flow measuring schemes, often are of complex design and/or provide highly inaccurate quantitative measurements for different reasons. With some systems, a measure of the cross-sectional area of the vessel is required together with blood velocity measurements, for use in calculating volumetric flow. With such arrangements, great difficulty often is encountered in obtaining accurate real-time cross-sectional area measurements.

SUMMARY OF THE INVENTION AND OBJECTS

An object of this invention is the provision of improved method and apparatus for the diagnosis of cardiovascular diseases, particularly in the carotid and femoral arteries.

An object of this invention is the provision of an improved combination pulsed B-scan ultrasonic imaging and pulsed Doppler system which is easily used for making accurate volume flow measurements.

An object of this invention is the provision of an ultrasound system of the above-mentioned type which includes novel display means to provide the operator with significant clinical data concerning the interior of an artery, or the like.

The above and other objects and advantages of this invention are achieved by use of separate focused B-scan and Doppler transducers within a mounting head containing acoustic transmission medium, such as water, and having a liquid-tight acoustic window therein for coupling to the subject under investigation. Asynchronously operated B-scan and Doppler signal transmitters supply recurrent different frequency pulses to the transducers for launching pulses of ultrasonic waves into the subject. The B-scan transducer is supported for recurrent scanning movement across the section of the interior of the object to be imaged, and the Doppler transducer is fixedly supported with the beam axis extending through the image plane of the B-scan system at a known, fixed, angle therewith. Separate B-scan and Doppler signal receivers are provided for processing the received B-scan and Doppler pulse signals reflected from discontinuities, particles, and the like, within the subject. In one operating mode a real-time B-scan display of the ultrasonic image is provided by a visual display means, together with a Doppler cursor signal which identifies the line along which signals from the Doppler transducers are received. By observation of the B-scan image and an associated A-scan display, the B-scan section image is located in a plane which is normal to the vessel axis, thereby positioning the axis of the Doppler transducer at a known angle relative to the vessel axis for accurate velocity measurements across the vessel. The depth and length of the Doppler cursor are adjusted to extend at least completely across the diameter of the vessel of the B-scan image display thereof.

With the Doppler transducer and cursor properly positioned, the system is switched to a second operating mode for operation of the Doppler system during which operation the Doppler receiver provides a plurality of output signals, each of which is proportional to tissue velocity at a different location along the beam axis. Except for novel gain control means; a Doppler system of substantially well known design may be employed to obtain the velocity signals proportional to tissue velocity along a line. One such system includes a transmitter for recurrent generation of a short burst of r.f. energy, say 5 cycles at 5 MHz. The transmitter may operate at a repetition rate of, say, 10 KHz. The generated signal is amplified by a transmitter amplifier whose gain is adjusted in accordance with both a front panel gain control setting, and front panel depth control setting. The amplified pulses are further amplified and then connected to the Doppler transducer through suitable switches, including a transmit/receiver switch, for pulse insonification of the subject.

Following the transmitted burst, echoes received by the Doppler transducer from insonified tissue are converted to voltage waveforms and amplified by an r.f. amplifier at the Dopper receiver. As with the transmitter amplifier, the gain of the receiver amplifier is adjusted in accordance with both the front panel gain control setting, and front panel depth control setting. Selective filtering, by a 2 MHz bandwidth matched filter removes unwanted noise, thereby improving the signal-to-noise ratio to the best possible degree. The resulting signal then is applied to a pair of quadrature r.f. mixers.

At the quadrature r.f. mixers, the received signal magnitude and phase are compared by two reference signals of constant amplitude and 90° relative phase. The resulting in-phase (I) and quadrature (Q) signals from the two mixers are termed range/phase signals.

They are stationary as long as the received echoes are from stationary tissue within the subject. However, if the echoes are received from moving tissues, such as blood, then the mixer output signals change with time. It is this change which is detected by the following circuitry.

Unwanted harmonics of the reference signals, and their associated sidebands, are removed from the range/phase signals by means of linear-phase low-pass filters, such as a pair of 2 MHz filters. A plurality of pairs of sample and hold circuits are included for sampling the filtered pair of range/phase signals from the quadrature r.f. mixers. In the present Doppler receiver sixteen pairs of sample and hold circuits are employed for measurement of tissue velocity at sixteen points along the Doppler transducer axis. The front panel depth control setting establishes the delay between the transmit burst and the instant that the first pair of sample and hold circuits samples the (I) and (Q) signals. A front panel span control setting establishes the delay between successive sampling by the pairs of sample and hold circuits, thereby establishing the distance between points at which velocity measurements are obtained. The frequency of each pair of signals, from the sixteen pairs of sample and hold circuits, is proportional to tissue velocity.

These sixteen pairs of signals again are filtered through thirty-two bandpass filters to remove both signals from stationary or nearly stationary tissues (very low frequencies below 50 Hz) and signals due to the sampling process (very high frequencies above 4.5 KHz). The resulting sixteen pairs of clean signals are frequency-to-voltage converted to provide sixteen slowly varying signals, the magnitude of which is proportional to tissue velocity, and the polarity of which is indicative of direction of tissue movement.

To produce the desired output-voltage-proportional-to-tissue-velocity signals sixteen frequency/power product detectors are employed each of which is responsive to a pair of the filtered signals. Different frequency/power product detectors for such use are well known. One such detector is disclosed in an article by M. V. Allen and J. D. Meindl entitled, "Center Frequency Estimation of Doppler Signals Using An Improved Quadrature Zero-Crossing Counter", 30th ACEMB, Los Angeles, CA., Nov. 5-9, 1977. By use of voltage comparator circuits, the frequency/power product detectors first produce thirty-two waveforms, each of which is proportional only to the zero crossings of the signals from the bandpass filters. The resulting sixteen pairs of "square" waves are then combined in a Quadrature Zero Crossing circuit, of the type disclosed in the above-mentioned Allen et al article, which produce a series of pulses (positive and/or negative). Sixteen 15 Hz linear-phase low-pass filters are used to integrate the pulses to produce the desired output voltage which is proportional to tissue velocity.

Those sixteen signals, each proportional to tissue velocity at a different location (i.e. tissue depth), are simultaneously sampled 30 times per second by sixteen sample and hold circuits. This sampling rate synchronizes the analog Doppler receiver of the Doppler system with computational and display subsystems which utilize the receiver outputs.

The sixteen analog velocity values from the sixteen sample and hold circuits are sent through a multiplexer to an analog-to-digital converter to be digitized. The digitized velocity signals then are fed to a computational computer and thence to a display computer for the real-time display of an accurately calibrated velocity profile of flow within the vessel. This calibrated velocity profile is displayed together with an A-scan display of data obtained from the line of data from the B-scan system corresponding to essentially the span of the Doppler sample volumes.

From each group of velocity values supplied to the computational computer, an instantaneous volume flow value is calculated using semi-annular area values based on the assumption of semi-circular symmetry of the vessel. The instantaneous flow volume is calculated as the sum of the product of each Doppler velocity signal and a corresponding area of a half annuli, centered at a calculated midpoint of the velocity profile. The resulting flow volume value is passed to said display computer where it is scaled and displayed as one point of a scrolling, or moving, waveform showing, say, two seconds of instantaneous volume flow. The scale factor of this display is made a function of the span control setting to allow both large and small flow rates to be observable on the scrolling display. In addition to the instantaneous volume flow calculations, the volume flow over the last complete cardiac cycle also is calculated and displayed as a numerical value. With the present arrangement the cardiac cycle is determined from the instantaneous volume flow values, thereby avoiding the need to obtain an EKG signal from the subject.

In another operating mode, the individual velocity profiles, and cardiac cycle volume flow values, are averaged over a plurality of cardiac cycles. The resulting averaged velocity profile data points are displayed together with the above-mentioned instantaneous volume flow values calculated over an interval of time of, say, two seconds. An operator-controlled switch allows velocity profiles from different parts of the cardiac cycle to be examined. A marker adjacent the instantaneous volume flow display indicates the temporal position in the cardiac cycle corresponding to the displayed velocity profile. In this operating mode, an A-scan display also is provided. The average value of the cardiac cycle volume flow also is displayed numerically.

The invention, as well as the above and other objects and advantages thereof, will become apparent from the following detailed description when considered with the accompanying drawings. It will be understood that the illustrated preferred embodiment of the invention included herein is by way of example only, and that the invention is not limited thereto. It is intended that other embodiments which suggest themselves to those skilled in the art shall fall within the spirit and scope of the appended claims.

BRIEF DESCRIPTION OF THE DRAWINGS

In the drawings, wherein like reference characters refer to the same parts in the several views:

FIGS. 7A and 7B show a fragmentary number of semi-circular and semi-annular areas associated with the velocity measurement points when different velocity mid-points are used in determining said areas;

FIG. 8 is a block diagram showing the display subsystem in greater detail; and

FIG. 9 is a simplified block diagram to further illustrate dependency of the gain of the Dopper system upon the setting of the front panel Doppler depth control.

Figure 1:
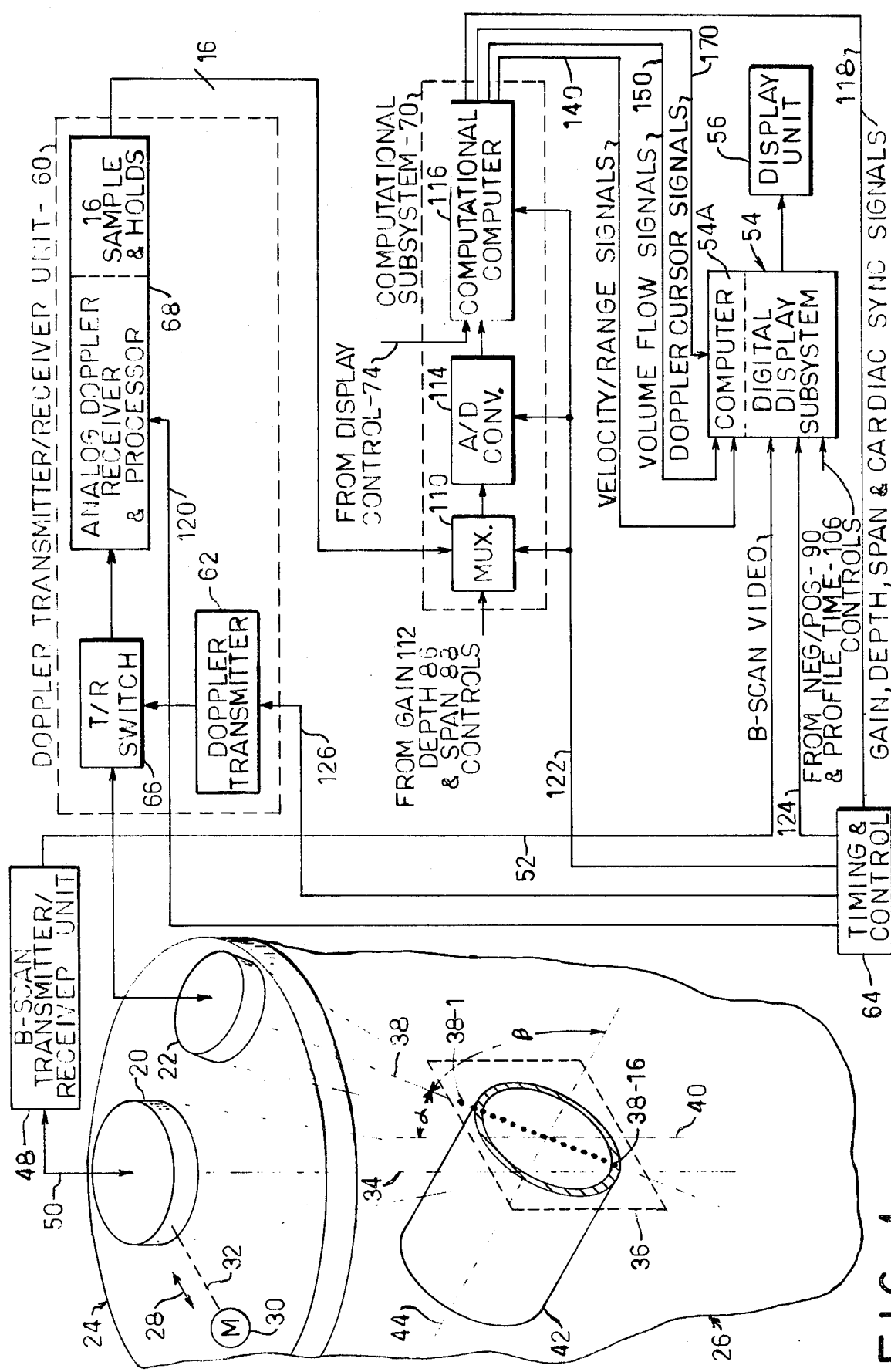
FIG. 1 is a simplified block diagram showing an ultrasonic imaging and volume flow measuring apparatus which embodies the present invention.

Reference first is made to FIG. 1 of the drawings wherein B-scan and Doppler transducer means 20 and 22, respectively, are shown mounted within a scanning head 24 carried at the end of an articulated arm, not shown,, for support over a subject or patient 26. The head contains a suitable acoustic transmission medium, such as water, for support of acoustic waves produced by the transducer means 20 and 22. A liquid-tight acoustically transparent window closes the lower end of the scanning head 24, through which window acoustic compressional waves generated by the transducer means are coupled to the subject 26, and through which reflected acoustical signals returned from the subject are coupled to the transducer means.

For purposes of description, and not by way of limitation, focused transducer means 20 and 22 are employed comprising, for example, lens-focused transducers. In the B-scan operating modes, the B-scan transducer 20 is recurrently moved back and forth in the direction of double-headed arrow 28 by a motor 30 connected to the transducer through mechanical linkage 32. The acoustic axis 34 of the B-scan transducer thereby is linearly scanned along the subject for B-scan imaging of a section 36 within the subject. The invention is not limited to use of a linearly scanned B-scan transducer. The B-scan transducer 20 could be moved in other fashions. For example, it could be rocked back and forth to produce the common sector scan.

With the illustrated arrangement, the Doppler transducer 22 is located at a fixed position, with the transducer axis 38 thereof intersecting the B-scan image plane 36 at a known fixed angle $\alpha$ on the order of, say, 25°. Additionally, the fixed Doppler transducer axis 38 intersects the image plane 36 at substantially the center of the linear sweep of the B-scan transducer 20. In FIG. 1, the Doppler transducer axis 38 is shown intersecting a line 40 extending along the center scan of the image plane 36. As is well understood, to make quantitative velocity measurements using Doppler techniques, the angle between the direction of flow and the acoustic beam axis must be known. With the present arrangement, this angle is established at a known, predetermined, angle by positioning the scanning head 24 such that the B-scan image plane 36 is normal to the direction of flow. For example, to properly orient the Doppler transducer 22 for quantitative velocity measurements of blood flow in vessel 42 shown in FIG. 1, the B-scan image plane 36 first is positioned normal to the axis 44 of the vessel, with the line 40 intersecting the vessel axis 44. When so positioned, it will be seen that the Doppler transducer axis 38 intersects the vessel axis 44 at an angle $\beta$ which is complementary to fixed angle $\alpha$. Consequently, with a fixed angle $\alpha$ of 25°, as suggested above, an angle $\beta$ of 65° is established between the direction of blood flow in the vessel and the Doppler transducer axis 38. It will be apparent, then that a measure of axial velocity is obtained by dividing velocity measurements obtained from along the Doppler axis 38 by the cosine of angle $\beta$.

A pulse B-scan transmitter/receiver unit 48, which may be of conventional design, may be used in the B-scan imaging portion of the novel system of this invention. As is well understood, the unit 48 includes a transmitter section for the recurrent generation of high frequency energy pulses which are supplied to the transducer 20 over line 50. The B-scan system may operate at a relatively high frequency of, say, 10 MHz, which is substantially optimal for this type of imaging. Focused ultrasonic wave pulses from the B-scan transducer 20 pass through the liquid medium and into the subject 26 for pulse insonification thereof. Echo signals received by the transducer 20 from discontinuities within the subject are converted to electrical signals which are supplied to the receiver section of the transmitter/receiver unit 48. The B-scan receiver is gated on after a delay period following generation of the last B-scan pulse for receiving echo signals from within a range of depths shown by the image section 36. As the transmitter 20 is periodically swept back and forth along its scan path by motor 30, signals for a two-dimensional B-scan display are provided at the output from the transmitter/receiver unit 48. Position sensing means, not shown, monitors the position of the B-scan transducer 20 and sends corresponding signals to a digital display subsystem, described below, so that a conventional B-scan image can be produced at the output of the system.

The B-scan video signal from the receiver of the transmitter/receiver unit 48 is connected over line 52 to a digital display subsystem 54, described in detail hereinbelow. In addition to the B-scan video signal from the B-scan transmitter/receiver unit 48, the digital display subsystem is provided with velocity/range, volume flow, and Doppler cursor signals which are obtained through use of the Doppler and computational portions of the combination system. Depending upon the selected display mode, selected signals are transferred from the digital display system 54 to a video display unit 56 for visual display thereof.

A pulsed Doppler transmitter/receiver unit 60, which also may be of conventional design, may be used to make the necessary blood velocity measurements. For example, a pulsed Doppler transmitter/receiver unit of the general type disclosed in the above-mentioned U.S. Pat. No. 4,141,347 and in the above-mentioned article entitled, "Pulsed Ultrasonic Doppler Blood-Flow Sensing" SU-17, pp. 170–185 (1979) by D. W. Baker, may be employed in the present system. The entire disclosures of said U.S. Pat. No. 4,141,347 and Baker article specifically are incorporated by reference herein. The system is designed to produce signals with minimum errors in order for the volume flow values to have diagnostic accuracies. In brief, the illustrated pulsed Doppler transmitter/receiver unit 60 is shown to include a transmitter 62 for recurrent generation of high frequency electrical energy pulses under control of timing and control unit 64, which pulses are supplied to the Doppler transducer 22 through a transmitter/receiver switch 66. As noted above, the resultant focused ultrasonic waves from the transducer 22 are transmitted through the liquid medium to the subject 26 for pulse insonification along the beam axis 38. The pulsed Doppler system may be operated at a frequency of, say, 5 MHz which is substantially optimal for Doppler operation involving blood flow in carotid and femoral arteries. It also is sufficiently separated from the B-scan frequency as to avoid interference between the B-scan and Doppler frequency pulse signals. The transmitter 62, under control of the timing and control unit 64, is operated to provide the transducer 22 with phase-coherent 5 MHz bursts of, say, 1 microsecond duration at a relatively high pulse repetition frequency of, say, 10 KHz.

With a 1 microsecond pulse width, range resolution on the order of 1.0 mm is provided. Lateral resolution, at focus, also is on the order of 1.0 mm. With this operation accurate velocity measurements may be made at spaced points along the Doppler beam axis 38. A relatively high pulse repetition frequency is used to allow Doppler shift frequencies up to 5 Khz to be accurately sensed. Such shifts result, for example, when the artery is becoming clogged.

Following transmission of an ultrasonic pulse by the Doppler transducer 22, echo signals from scatterers within the subject 26 are received by the transducer and the electrical signal output therefrom is supplied through the transmit-receive switch 66, now in receive condition, to an analog doppler receiver and processor unit 68. The analog Doppler unit 68 includes a plurality of output channels, here sixteen, the signal outputs from which are related to the Doppler frequency shift of echo signals received from sixteen equally spaced measuring points 38-1 through 38-16 along the Doppler transducer axis. Sixteen sample and hold circuits at the output of the analog Doppler unit 68 provide temporary storage for the sixteen analog output signals. These sixteen analog output signals, proportional to the mean value of tissue velocity at the associated measuring points, are supplied to a digital computation subsystem 70 for use in calculating instantaneous volumetric flow and volumetric flow per cardiac cycle in the vessel 42 in a manner described below. Obviously, fewer or additional Doppler output channels than the sixteen illustrated may be employed. It here will be noted that depth and span control means, under operator control, are provided whereby the analog Doppler receiver and processor unit 68 may be operated to provide velocity signals from different depths and from along different length portions of the transducer axis 38.

Figure 2A:
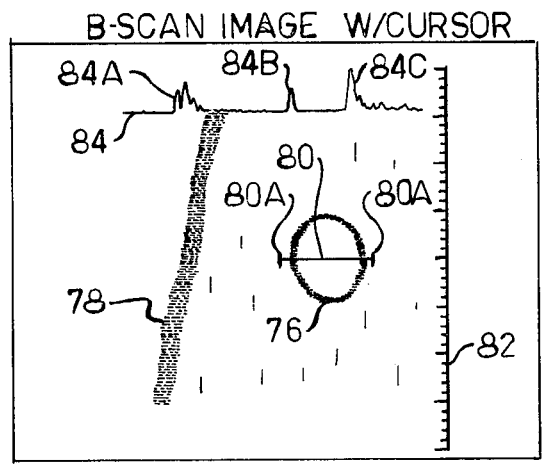
FIGS. 2A, 2B and 2C are diagrammatic views of the face of the visual display means showing three of the four display modes provided by apparatus of this invention.
Figure 3:
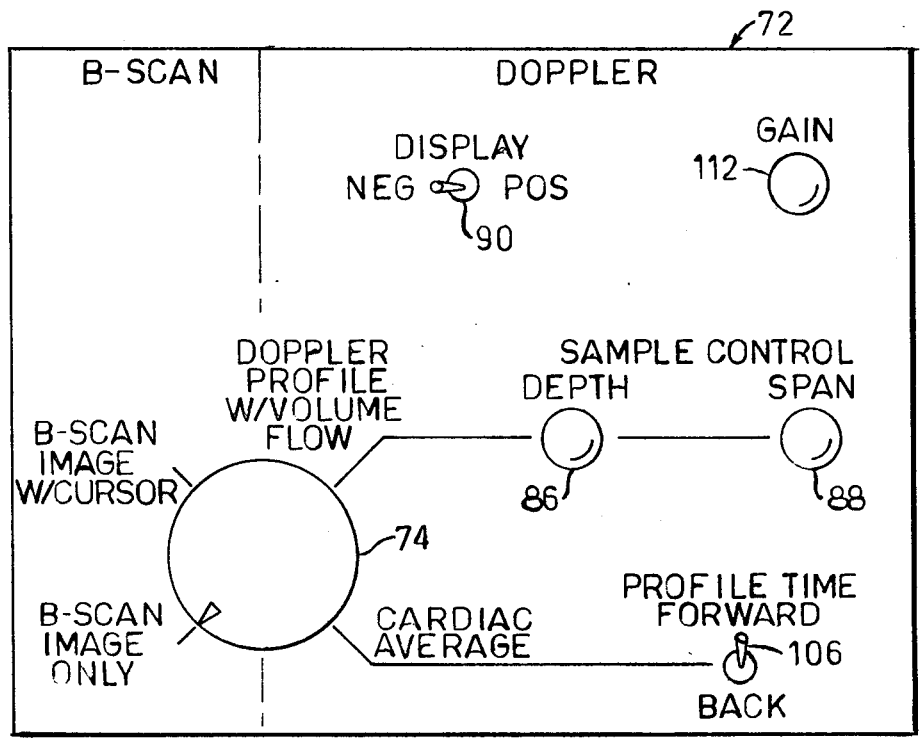
FIG. 3 is a view of the front panel of the ultrasonic apparatus of FIG. 1 showing various manual control elements for use by the operator.

System operating controls included at the front panel 72 of the present apparatus are shown in FIG. 3, to which figure reference now is made. There, B-scan and Doppler control sections are shown. A multiposition switch 74 is positioned intermediate the two sections, for control of the B-scan and Doppler system, and mode of display. As will be noted, two different operating and display modes are provided for both B-scan and Doppler systems. At one switch position labeled B-scan image only, the conventional display of B-scan only is provided. At the second B-scan operating mode, labeled B-scan image w/cursor, the B-scan image is displayed, together with a cursor identifying the section along which Doppler velocity signals are obtained when the system is switched to a Doppler operating mode, and an associated A-scan line. An example of the display provided at the B-scan image w/cursor setting of switch 74 is shown in FIG. 2A. There, the illustrated B-scan display includes a transverse sectional image 76 of the common carotid artery. The skin 78 also is clearly shown in the B-scan image since the reflection therefrom is large. As is well understood, the transmitted ultrasonic wavefield is reflected by irregularities and discontinuities encountered thereby, and the discontinuity provided by the skin is great. Blood, however, is less reflective than the surrounding tissue and reflected signals therefrom are below the minimum sensitivity of the B-scan receiver. The blood appears as a light area in the drawings. In practice, the light and dark areas of the drawings would be reversed unless the intensity control signal is inverted to provide for the illustrated type of display. That is, the arterial lumen would appear as a dark area on the screen since substantially no reflected B-scan signals are obtained therefrom. A cursor 80 is included in the display to indicate the line along which the Doppler velocity signals are to be acquired when the system is switched to one of the Doppler operating modes. The cursor ends are marked by short vertical marks 80A, 80A for ease in locating the cursor and identifying the ends thereof. These marks represent the positions of the first and sixteenth Doppler sample points. For accurate velocity measurements of blood flow in the artery, the cursor is positioned to extend substantially diametrically across the entire artery image diameter, as illustrated in FIG. 2A, and should always include all of the artery as the artery moves and expands during the cardiac cycle. Excessive cursor length only places fewer of the sixteen Doppler sample points within the flow region resulting in a greater error in the final volume flow values, but does not prevent proper operation of the system. Front panel depth and span controls 86 and 88 (FIG. 3) are used to set the depth and length of the cursor 80 during operation in the B-scan with cursor mode illustrated in FIG. 2A. As will become apparent hereinbelow, the settings of depth and span controls 86 and 88 also establish the depth of the first Doppler sample point 38-1 and the span between Doppler sample points 38-1 and 38-16, respectively, when operation is switched to a Doppler mode.

The B-scan with cursor display of FIG. 2A also includes calibrated tick marks 82 along the right side thereof for use in distance measurements. For purposes of illustration, the spacing between adjacent tick marks identifies a distance of 0.1 cm. With the illustrated arrangement, a section which is substantially 3.0 cm wide by 4.0 cm deep is imaged by the B-scan system. Also, it will be noted that an A-scan display 84 is included in this mode of operation which simply comprises the display of data obtained by the B-scan system from along a single scan line when the B-scan transducer 20 is positioned at the center of the scan, in line with line 40 shown in FIG. 1. As seen in FIG. 2A, waveform 84A of the A-scan display is produced by reflections from the skin, and waveforms 84B and 84C are produced by reflections from the walls of the vessel.

Figure 2B:
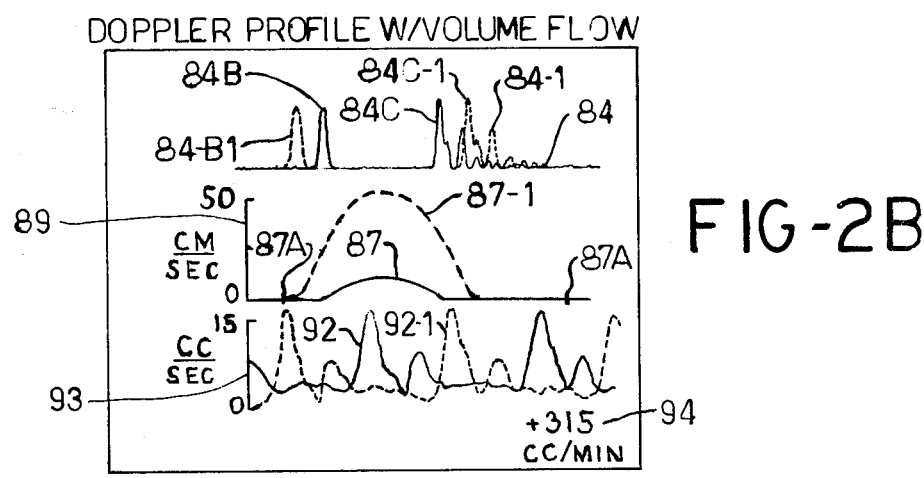

As noted above, with the illustrated system, the B-scan with cursor display shown in FIG. 2A provides a convenient means by which the Doppler transducer 22 may be positioned at a predetermined, known, angular position relative to the vessel axis 44. Now, when the system is switched to a Doppler operating mode, Doppler mean frequency signal values which are obtained from points 38-1 through 38-16 along the Doppler transducer axis provide, when scaled correctly, an accurate, quantitative, measure of tissue velocity in the direction of axis 44 of the vessel 42. With mode selector switch 74 in the Doppler Profile w/Volume Flow position (FIG. 3) a display of the type shown in FIG. 2B is provided at the face of the cathode ray tube included in the display unit 56 (FIG. 1). As seen in FIG. 2B, this display includes a portion of the A-scan line 84 shown in FIG. 2A. In particular, a portion of A-scan which spans a slightly greater distance than the line along which Doppler velocity signals are obtained now is displayed. In the Doppler operating mode, the B-scan transducer 20 is locked in a center position of the scan, by means not shown, wherein the beam axis 34 is axially aligned with line 40 at the center of the B-scan image plane 36. In this operating mode, data for A-scan display is updated ten times per second. As noted above in the description of the B-scan imaging with cursor display illustrated in FIG. 2A, the cursor 80 identifies the line along which Doppler velocity signals are obtained when operating in the Doppler mode.

The line along which Doppler velocity signals are received and processed is adjustable both in depth and in length, or span, under control of front panel control means 86 and 88, respectively. The range gate depth control 86 is used to control the time delay between the transmission of a Doppler pulse signal and the operation of the Doppler receiver to acquire a Doppler velocity signal from the first measuring point 38-1. The range gate span control 88 controls the rate at which measurements are made at the sixteen points for control of the spacing between Doppler velocity measurements. As noted above, these Doppler range gate depth and span controls 86 and 88, respectively, also serve to set the depth and length of the cursor 80 during operation in the B-scan with Doppler cursor mode. Generally, these controls are operated only while in the B-scan with cursor operating mode, during which time the scanning head 24 is properly oriented relative to the vessel 42 under examination, and the cursor 80 is positioned to extend across the vessel diameter. When properly positioned the control 74 is switched to the Doppler profile with volume flow setting and the scanning head is held in fixed position relative to the subject during Doppler operation to maintain the angular position between the Doppler transducer axis 38 and vessel axis 44 required for making quantitative velocity measurements. The A-scan display in the Doppler profile with volume flow operating mode (FIG. 2B) is used by the operator to see that alignment is maintained. Any subject movement or misalignment can be observed, and the system switched back to the B-scan image with cursor operating mode (FIG. 2A) for realignment.

In a system which has been built and tested, the Doppler "window" provided by depth and span control means 86 and 88, respectively, is adjustable in depth from the skin surface to greater than 3 cm. The range gate spacing, under control of span control means 88, is adjustable to obtain velocity measurements along a total/span ranging from 3.75 mm to 25.5 mm. A total of eight distinct spans are provided within this range, with the eight different spacings between the sixteen measurement points ranging from 0.25 mm to 1.7 mm. Obviously, the invention is not limited to such an embodiment.

From the Doppler measurements obtained from the sixteen points 38-1 through 38-16, quantitative velocity measurements are readily calculated by the computation subsystem 70 since the angle $\beta$ between the Doppler transducer and vessel axes is known. These velocity measurements are displayed beneath the A-scan display 84 to provide a velocity versus distance profile 87. Marks 87A on this display identify the end points 38-1 and 38-16 between which the sixteen velocity measurements are obtained. Since accurate, quantitative, velocity values are obtained, a calibrated velocity scale 89 is provided. In FIG. 2B, the velocity scale extends to 50 cm/sec. although velocity as high as 80 cm/sec. can be displayed before exceeding the display capability. Velocity values ranging from 0.625 cm/sec. to 80 cm/sec. can be resolved. To provide for a smooth display of substantially interconnected points, the scaled velocity data is displayed with a plurality of interpolated points between each measured velocity point.

The velocity data collection and processing hardware accommodates blood flow in either axial direction. In FIG. 2B, blood flow in one axial direction is indicated by use of a "positive" velocity scale which extends upwardly from the zero point at the intersection with the distance axis. Blood flow in the opposite direction is indicated by use of a "negative" velocity scale which extends downwardly from the zero point at the intersection with the distance axis. For this display, the distance axis extends horizontally at a height at substantially the tick mark labeled "50" on scale 89. Control switch 90 (FIG. 3) at the front panel is used to establish which of the two scales, i.e. negative or positive, is displayed.

In addition to the A-scan display 84 and Doppler profile 87, the display of FIG. 2B also includes a waveform 92 showing instantaneous volume flow. A novel method of computing instantaneous volume flow from the sixteen velocity measurements obtained each cycle of operation of the Doppler computation system is described in detail hereinbelow. For present purposes it will be understood that with the sixteen velocity measurements, and a knowledge of the approximate location and spacing between the measuring points, an accurate calculation of instantaneous volume flow is obtained. With operation of the Doppler calculation system at a repetition frequency of 30 cycles per second, 30 instantaneous volume flow values per second are obtained.

Display 92 comprises a scrolling display of 60 successive instantaneous volume flow values such that a real time display of instantaneous volume flow values obtained over a period of the past two seconds is provided. As new volume flow values are calculated, they are added to the right end of the display 92 to provide for a display which appears to travel from right to left across the face of the display tube. In FIG. 2B, a calibrated instantaneous volume flow scale 93 which extends from 0 to 15 cc/sec. is shown. Eight different instantaneous volume flow scales are provided having maximum flow values ranging from 0.03 cc/sec. to 80 cc/sec. The volume flow scale employed is dependent upon the span over which the Doppler velocity measurements are obtained which, as described above, depends upon the setting of span control means 88. Blood volume flow in larger diameter vessels generally is greater than in smaller diameter vessels due to the larger cross-sectional area. Therefore, the largest volume flow scale is associated with the setting for the largest span. With this arrangement, automatic proper scaling of the volume flow waveform is provided.

In addition to the instantaneous volume flow calculations, and scrolling display 92 thereof, the volume flow over a cardiac cycle also is calculated and displayed as a numerical value 94 at the lower right-hand corner of the display shown in FIG. 2B. The volume flow over a cardiac cycle is calculated by summing the instantaneous volume flow values over the cardiac cycle and then dividing the sum by the number of flow values in the cycle. The resulting number is scaled and displayed. A plus or minus sign preceeds the display, indicating the relative direction of flow in the vessel. Each cardiac cycle the display of cardiac cycle volume flow is updated.

To illustrate the real-time nature of the combination A-scan 84, quantitative velocity versus distance profile 87 and instantaneous volumetric flow 92 display of FIG. 2B, values obtained at a different point in the cardiac cycle of the subject are illustrated in the broken line showings 84-1, 87-1 and 92-1 included in FIG. 2B. The broken line displays are provided as a result of measurements obtained when blood flow is substantially maximum, at about systolic blood pressure. In the broken line showing, the A-scan peaks 84B-1 and 84C-1 are further spaced apart than peaks 84B and 84C showing dilation of the vessel under increased pressure conditions. The velocity versus distance profile 87-1 reaches a much larger velocity value and is wider due to the greater vessel diameter, and the instantaneous volumetric flow display 92-1 is shown moved to the left approximately one-half a cardiac cycle.

Figure 2C:
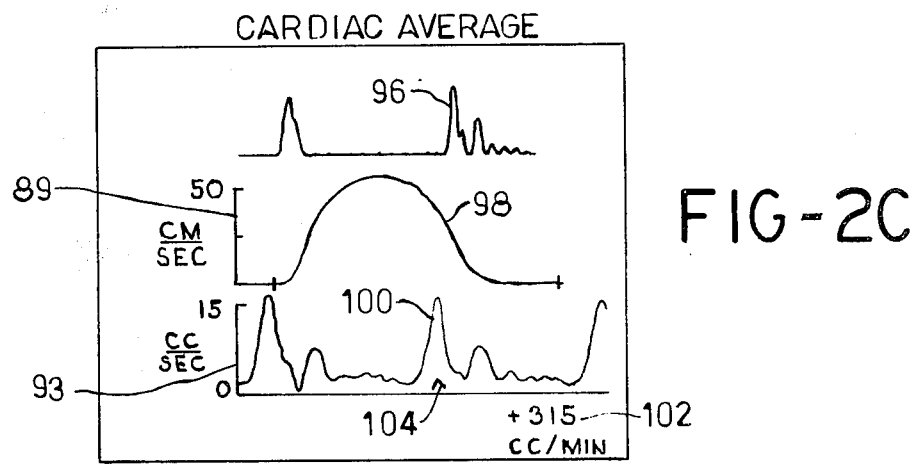

A second type of Doppler information display is shown in FIG. 2C, which display is provided when the mode selection switch 74 (FIG. 3) is switched to the Cardiac Average position. This is a stationary display which, as seen in FIG. 2C, includes an A-scan display 96, an average velocity versus distance profile 98, an average instantaneous volumetric flow display 100, and a numerical display 102 of average volume display, all but the A-scan display being averaged over eight cardiac cycles. A movable marker, or pointer, 104 associated with the average instantaneous volumetric flow display 100, and movable along the longitudinal axis thereof, identifies the temporal point in the cardiac cycle at which values for display of the average velocity versus distance profile 98 is obtained. In this mode, the last-acquired A-scan line is displayed, which display 96 remains stationary. Also, the average instantaneous volumetric flow display 100 is stationary and provides for the display of a two second period. The numerical display 102 of average cardiac cycle volume flow remains constant in this display mode and is the average of eight cardiac cycle values. Once velocity measurements are made over a period of eight cardiac cycles, and the necessary calculations performed and resultant values stored, velocity profile displays obtained from a selected point in the cardiac cycle may be displayed for detailed study by the operator.

The point in the cardiac cycle selected for display, identified by the movable pointer 104, is under control of Profile Time switch 106 at the front panel 72. The switch is movable from a central, off, position to a forward or back position for stepping the pointer 104 either to the left or right along the axis of the average volume flow waveform 100. In this operating mode, the operator may examine the velocity profile and volume flow present at any desired point in the cardiac cycle. Since values for display are obtained by averaging values obtained over a plurality of cardiac cycles, higher accuracy than real-time quantitative displays are provided. Calibrated scales 89 and 93 corresponding to scales included in the display of FIG. 2B also are employed in the FIG. 2C display. It will be apparent, then, that with quantitative measurements provided by this invention, the invention not only is adapted for diagnostic use with individual subjects, but it also is adapted for use in screening subjects in which case variations from normal velocity and volume flows are detected for follow-up diagnosis and treatment.

Reference again is made to FIG. 1 wherein the computational sub-system 70 is shown to include an analog multiplexer 110 to which the sixteen analog velocity signals from the sample and hold circuits in the output of Doppler receiver 68 are supplied. Three other analog signals are supplied to the input of multiplexer 110, including a gain control signal which is established by setting of Doppler gain control means 112 at the front panel, and depth and span control signals obtained from the depth and span control means 86 and 88, respectively. The multiplexer output is connected to an analog-to-digital converter 114 for conversion of the velocity, gain, depth and span signals to digital form for use by a digital computational computer 116. in practice, the computational computer 116 simply may comprise a microcomputer, such as a Z80 microcomputer.

From the velocity signals obtained from the Doppler receiver, a cardiac synchronization signal is derived in a manner described below. The digital gain, depth, and span control signals, together with the cardiac synchronization signals, are connected over line 118 to the timing and control unit 64. Gain control signals from the timing and control unit 64 are supplied over line 120 to the Doppler receiver, and over line 126 to the Doppler transmitter, for gain control of R-F amplifier means included in the Doppler receiver input and Doppler transmitter output, respectively. Depth control signals are supplied over line 120 to the analog Doppler receiver and processor for control of the time delay between operation of the Doppler transmitter 62 and the time the receiver and processor 68 is operated to obtain the first velocity signal from measuring point 38-1. (Depth control signals also are supplied to the Doppler receiver and Doppler transmitter for gain control thereof, in a manner described below.) Span control signals supplied to the Doppler receiver and processor 68 control the rate at which the sixteen receiver outputs are sampled to obtain the sixteen velocity signals, which rate, then, determines the spacing between measurement points and, therefore, the span over which the velocity signals are obtained. Also, timing and control signals from the unit 64 are supplied to the computational subsystem 70 over line 122 and to the Digital display subsystem 54 over line 124.

The use of depth control signals for gain control of the Doppler transmitter and receiver units is functionally illustrated in FIG. 9, to which figure reference now is made. In FIG. 9, the gain control 112 controls the gain of both the Doppler transmitter 62 and receiver 68; the gain of both the transmitter and receiver being controlled in the same direction with changes in the setting of gain control 112. As seen in FIG. 9, the depth control 86, not only controls the range, or depth, at which velocity signals are obtained, but also controls the gain of both the transmitter 62 and receiver 68. As noted above, with increased depth settings of depth control means 86, the gain of both the Doppler transmitter and Doppler receiver is increased.

As is well understood, ultrasonic pulses are attenuated in travel through tissue; pulses reflected from scatterers further within the subject experiencing the greatest attenuation. It is common practice to compensate for such difference in attenuation by time variable gain amplification of received signals. In the present use of the Doppler system, wherein velocity measurements are obtained from across an artery, the difference in attenuation of signals received from the opposite end points 38-1 and 38-16 is relatively small since attenuation in blood is relatively small. Therefore, instead of using time variable gain amplification, gain is controlled by the setting of the depth control means 86. Once the gain control 112 is set for proper operation of the Doppler transmitter/receiver system, further adjustment thereof generally is not required even through the system is operated at different depths, since the depth control setting provides the necessary gain compensation. Although gain control of both the Doppler transmitter and Doppler receiver is shown in FIG. 9, it will be apparent that gain control of either one or the other thereof may be employed, instead of both.

CARDIAC SYNCHRONIZATION

Both Doppler operating modes require use of a cardiac synchronization signal. This signal may be supplied externally, as from an EKG signal, or it may be internally generated in the following manner.

Figure 4:
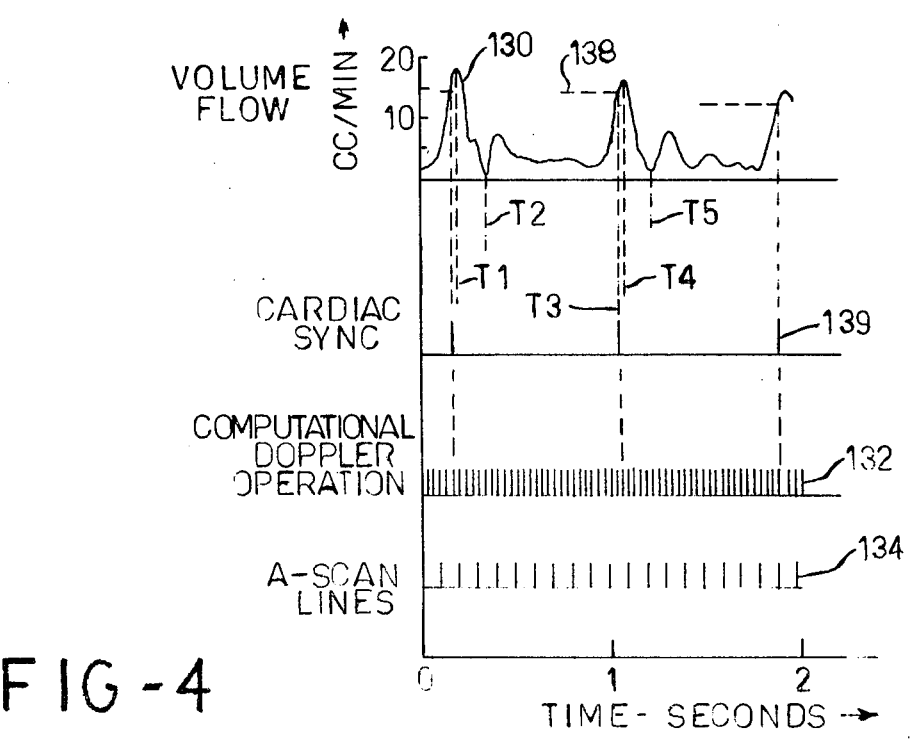
FIG. 4 are waveform and timing diagrams for use in explaining the operation of the present apparatus.

With the present arrangement, cardiac synchronization signals are derived from volume flow signals computed by computational computer 116. Reference is made to the waveforms of FIG. 4 of the drawings for an explanation of the method by which cardiac synchronization signals are obtained from the volume flow values. In FIG. 4, the upper waveform 130 is a plot of volume flow versus time, which waveform is similar to waveform 92 included in the display shown in FIG. 2B, described above. The method of calculating volume flow is described below. In FIG. 4, the Doppler transmitter output is identified by reference numeral 132, and the A-scan lines, obtained from the B-scan receiver, are identified by reference numeral 134. As noted above, the B-scan and Doppler systems operate asychronously, with the Doppler computation system operating at a repetition rate of substantially 30 operations per second, and A-scan lines being acquired, and displayed, at a rate of substantially 10 per second.

For each cardiac cycle the maximum and minimum values are determined. In FIG. 4, the maximum and minimum values for the first cardiac cycle are seen to occur at times T1 and T2. The difference between the maximun and minimum values is calculated, and a threshold value equal to the minimum plus ¾ of said difference is established, which level is identified by reference numeral 138 in FIG. 4. Now, when the instantaneous volume flow value crosses this threshold, at time T3, a cardiac synchronization signal 139 is produced which, as described above, is supplied over line 118 to the timing and control unit 64. A new threshold is established each cardiac cycle using the maximum and minimum volume flow values from the previous cycle in the manner described above. The rising edge of each pulse of blood volume is steep and relatively noise-free and, therefore, relatively easily and accurately sensed.

To prevent false triggering, a time out period is provided after each cardiac synchronization pulse. During this time, the synchronization circuit is not sensitive to signals passing the threshold. This period is approximately ⅓ sec. therefore providing for operation up to 180 beats per minute which, of course, is sufficiently high for use with any human subject.

Also, if no synchronization signal is sensed within 2 seconds (30 beats/minute minimum rate), a "synchronization" pulse is generated so that the cardiac volume flow numeric is updated. This is useful for measurements of steady venous flow on small diameter veins where no synchronization pulse is obtained, or needed, because flow is steady and any averaging period provides the correct volume flow value.

By using an adaptive threshold, operator control of the threshold level is not required to accomodate subjects with varying or different maximum volume flow rates. Also, by employing volume flow calculations to derive cardiac synchronization signals, there is no need to produce such signals through use of a cardiac R-wave detector, or the like, supplied with electrocardiograph signals obtained from electrodes attached to the subject.

At the timing and control unit 64, the cardiac synchronization signal 139 essentially delays the sampling of the output of the Doppler detectors by the 16 sample and hold circuits in the output of the analog Doppler receiver and processor 68 once each cardiac cycle in an amount necessary to provide that the velocity measurements are obtained at corresponding points in successive cardiac cycles.

The above-described synchronization is required for accurate calculation of volume flow over a cardiac cycle which value is displayed as a numerical value 94 when operating in the Doppler profile w/volume flow mode. This synchronization of the 30 Hz Doppler computation period (reference numeral 132 of FIG. 4) with the cardiac cycle (reference numeral 130 of FIG. 4) also allows velocity profiles from the same position in a plurality of cardiac cycles to be averaged together to provide data for display 98 shown in FIG. 2C. The resulting averaged profile data points exhibit lower variance and, therefore, represent a more accurate estimate of actual blood velocity in the vessel under observation than if no averaging was provided. Similarly, more accurate values for the average instantaneous volume flow display 100, and numerical display 102 of average volume flow per cardiac cycle are provided by this synchronization of Doppler operation with the cardiac cycle.

VELOCITY SIGNAL PROCESSING AND DISPLAY

As described above, in the B-scan image with cursor operating mode, the Doppler transducer 22 is positioned such that the Doppler transducer axis 38 intersects the vessel 42 at a known angle β relative to the vessel axis, and the cursor 80 is positioned, under control of depth and span control means 86 and 88, respectively, to extend diametrically across the vessel image 76 (FIG. 2A). Now, when switched to the Doppler Profile with Volume Flow mode, sixteen analog signals proportional to the instantaneous blood velocity at points 38-1 through 38-16 across the vessel 42 are produced at the output from the analog Doppler receiver and processor 68. These signals are digitized and supplied to the computational computer. With the Doppler computation system operating at 30 repetitions per second, a set of sixteen velocity signals are provided every 33.3 milli-seconds. The Doppler receiver gain information, together with the depth and span data, also is digitized and supplied to the computational computer 116 where the set of sixteen velocity values is scaled. The sixteen scaled digital velocity values, together with the depth and range information, are connected over line 140 to the digital display subsystem 54. Ten interpolated points between adjacent velocity values are calculated at the digital display subsystem utilizing a computer 54A included therein. The velocity signals, together with the interpolated points, are transferred to the display unit 56 for display at the face of the cathode ray tube included therein of the velocity profile 87, as seen in FIG. 2B.

INSTANTANEOUS VOLUME FLOW CALCULATION

For each velocity data set (comprising the sixteen velocity signals obtained from points at known spaced distances along the Doppler transducer axis) an instantaneous volume flow value is calculated by the computational computer 116 using an algorithm based on an assumption of semi-circular symmetry of the vessel 42. While vessels do not always have a circular cross-section, this assumption produces very low errors in the case of arteries which are usually substantially rigid and circular in cross section. Diseased arteries with plaque deposits demonstrate compromised lumens which are distortions of circularity that can frequently be fitted by two semi-circular areas of different radii. The assumption of semi-circular symmetry better fits these diseased arteries than an assumption of circular symmetry would. Thus, greater accuracy is also achieved is diseased arteries utilizing the present invention.

Figure 5:
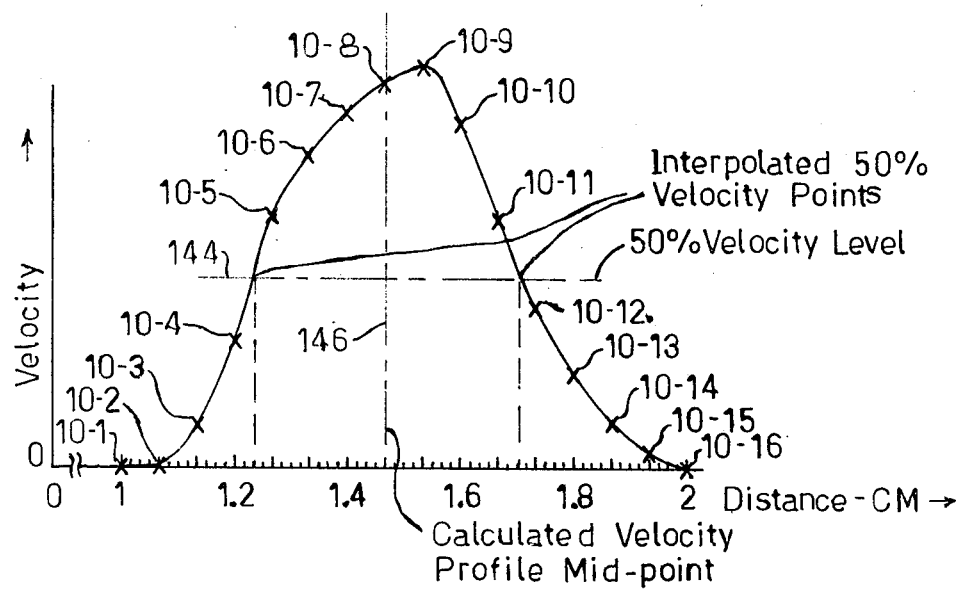
FIG. 5 is a plot of velocity versus distance for a set of instantaneous velocity measurements provided by the Doppler subsystem for use in explaining calculation of instantaneous volume flow.

The algorithm first finds the midpoint of the velocity profile represented by the velocity data set. Reference is made to FIG. 5 for use in explaining the midpoint calculation where a plot of the sixteen velocity signals, identified by reference numerals 10-1 through 10-16, versus distance is shown. With the illustrated span setting, the velocity measurements are obtained over a span of 1 cm. First, the peak magnitude signal of the sixteen velocity signals is determined. In the velocity data set of FIG. 5, signal 10-9 is seen to be the largest. From the peak magnitude the 50% magnitude value is calculated, which, in FIG. 5 is identified by line 144. In FIG. 5, the 50% velocity level is seen to extend between velocity signals 10-4 and 10-5 and between velocity signals 10-11 and 10-12. The two distance points corresponding to the 50% points in the velocity profile are then found to within $\pm \frac{1}{8}$ of the distance between adjacent velocity measurement points. These points, which are calculated by using linear interpolation between the data points, are located at a measuring point or at one of three equally spaced points between measuring points. In FIG. 5 the one 50% point is seen to lie midway between the 4th and 5th measuring points, and the other 50% point is seen to lie midway between the 11th and 12th measuring points along the distance scale.

Now, the profile distance midpoint is calculated as the mean of the two interpolated 50% distance points. With the set of velocity signals shown in FIG. 5, the profile midpoint, at line 146, lies directly at the measuring point at which the velocity signal 10-8 was obtained. It here will be noted that this calculated profile midpoint often is not located at the point at which the peak velocity signal was obtained, which in FIG. 5 comprises velocity measurement 10-9. By using interpolated 50% velocity points of the velocity profile to calculate the profile midpoint, a more accurate calculation of instantaneous volume flow, in the manner now to be described, is made possible.

Figure 6:
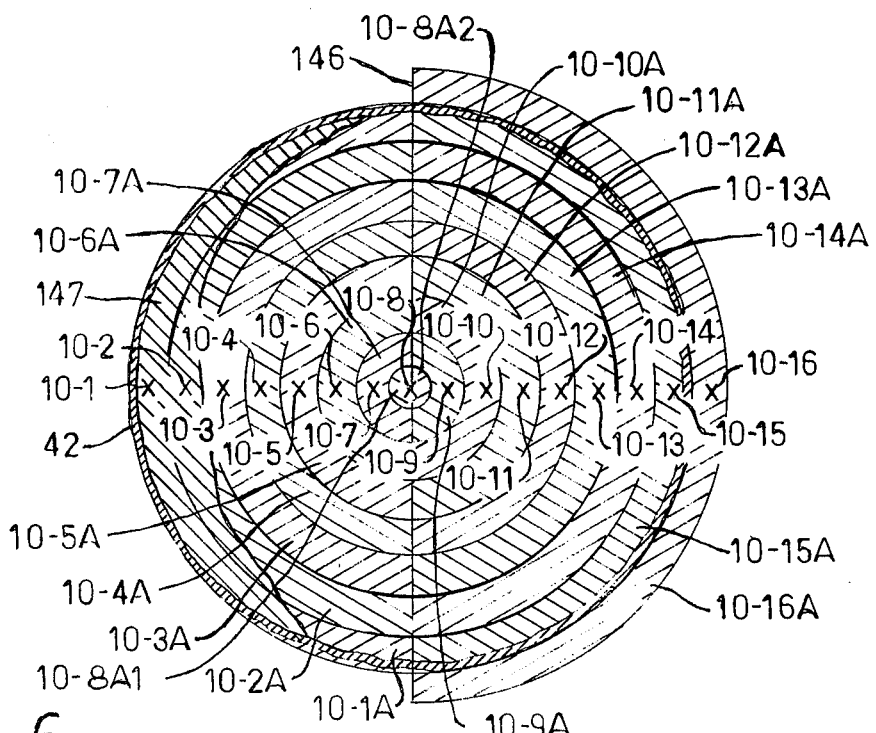
FIG. 6 is a transverse sectional view of a vessel showing semi-circular and semi-annular areas associated with the Doppler velocity measurement points.

Reference now is made to FIG. 6 of the drawings wherein there is shown a cross-sectional view of the vessel 42 together with points across the diameter thereof for which velocity signals 10-1 through 10-16 have been obtained. Also, the line 146 is shown perpendicular to the line of velocity signal points, which line extends through velocity signal point 10-8, the calculated mid-point. Plaque 147 is shown at the vessel wall. Instantaneous flow volume Q ($t_j$) at time $t_j$ is calculated as the sum of the product of each velocity value and a corresponding half annulus area whose arc is centered at the calculated profile midpoint and whose width is centered on the velocity measurement point. In FIG. 6 these areas are identified by reference characters 10-1A through 10-16A. One velocity signal 10-8 is shown associated with two areas 10-8A1 and 10-8A2 at opposite sides of the mid-point.

$$Q(t_j) = \sum_{I=1}^{16} V_I(t_j) \cdot A_I(t_j) \quad (1)$$

where V and A are values of velocity and area, respectively, at sample time $t_j$.

The calculated instantaneous flow volume value is scaled and transferred over line 150 from the computational computer 116 to the digital display subsystem 54 for display at display unit 56 as one point of the scrolling waveform 92 shown in FIG. 2B. As noted above, the instantaneous flow volume value is added to the right end of the scrolling waveform 92 which displays two seconds of instantaneous volume flow values. Also, as noted above, the scale factor for this display is a function of the span control setting to allow for both large and small flow rates to be observable on the scrolling display.

As described above with reference to FIG. 5, the two 50% points in the velocity profile are determined to be at a measurement point or at any one of three points between measurement points. It will be understood, then, that the midpoint of a particular velocity profile may lie at one of four positions relative to nearest measurement point. In particular, the measurement point and midpoint may be colocated, as illustrated in FIGS. 5 and 6, or separated by $+\frac{1}{4}$, $\pm\frac{1}{2}$ or $-\frac{1}{4}$ the distance between data samples. FIGS. 7A and 7B illustrate situations wherein the velocity profile midpoint is located $\frac{1}{2}$ the distance between data samples, and $\frac{1}{4}$ the distance between data samples from the nearest data sample, respectively. Obviously, the invention is not limited to this specific interpolation. Interpolation to better than or worse than $\pm \frac{1}{4}$ of a sample space may be employed, if desired.

Reference now is made to FIG. 7A wherein, for purposes of ilustration, the velocity profile midpoint, at line 146, is located midway between the measurement, or data sample, points 10-8 and 10-9. In this situation, it will be noted that half annuli of corresponding area are included at opposite sides of line 146. Instantaneous flow value through any given area is obtained, as described above, by multiplying the area by the corresponding velocity value. Flow through the sixteen individual areas are summed to obtain an instantaneous volume flow value which is added to the scrolling display 92. In the situation illustrated in FIG. 7A, it will be seen that the semiannular areas are uniquely assigned, one to a measurement point.

Now referring to FIG. 7B, the line 146 identifying the calculated midpoint of the velocity profile is shown at a distance of $\frac{1}{4}$ the distance between data samples from data sample 10-9. In this situation it will be noted that half annuli of unequal area are provided at opposite sides of the midpoint. Again, instantaneous flow values are calculated from corresponding velocity and area values, and the flow values are summed for display. In the situation illustrated in FIG. 7B, it will be seen that the smallest semiannular areas on each side of line 146 are combined to form area 10-9A.

Since the calculation of the midpoint of the velocity profile is limited to specific points along the line of measurement, areas of half annuli centered at said midpoints may be calculated and values thereof stored in the memory of the computational computer 116 for use as required. As noted above, eight different span settings are possible, each of which results in different area values. A normalized set of half annuli areas is used and appropriate scale factors are multiplied at the end of the entire calculation to account for the span setting.

In use, it is desirable to locate the cursor 80 and, consequently, the line along which velocity measurements are obtained, such that the measurement line extends across the vessel, with the center of the line at, approximately, the center of the vessel. If the line is not substantially centered, it will be apparent that the calculated profile midpoint may be located adjacent one end of the measurement line. For example, the velocity midpoint may be located midway between measurement points 10-3 and 10-4. In this case three half annular areas would be located at one side of the midpoint, and thirteen at the other side. It will be apparent, then, that a sufficient number of area values must be stored to accommodate situations wherein the calculated midpoint is adjacent either end of the line of velocity measurements. As long as the profile is narrow so that substantially all of the profile falls in the cursor length, although not centered, the volume flow estimate calculation will be correct. However, it is desirable to have a maximum number of Doppler samples within the flow of blood to reduce the variance in the volume flow estimate.

CARDIAC CYCLE VOLUME FLOW

An noted above, in addition to instantaneous volume flow calculations, the computer 116 also is used to calculate the volume flow over a cardiac cycle. The calculation of a cardiac cycle using the volume flow measurements and an automatically variable threshold was described with reference to FIG. 4. Volume flow $Q(t_c)$ over a cardiac cycle is readily calculated by computational computer 116 simply by accumulating the instantaneous flow values $Q(t_j)$ over the cardiac cycle and then dividing by the number of data sets in the cycle. An expression for volume flow per cardiac cycle is:

$$\overline{Q}(t_c) = \frac{\sum_{j=1}^{N} Q(t_j) + Q(t_{c-1}) \times M/8}{N + M/8} \quad (2)$$

where N is the number of whole sets of instantaneous volume flow values in the cardiac cycle and M is the number of ⅛th's of a sample period at cardiac synchronization to align the sampling points. The calculated value is scaled and supplied over line 150 to the digital display subsystem 54 to provide for numerical display 94 shown in FIG. 2B.

VELOCITY PROFILE AVERAGING

In the Cardiac Average setting of mode selector switch 74 (FIG. 3) the display illustrated in FIG. 2C is provided which includes a display 98 obtained by averaging individual velocity profiles over a plurality of cardiac cycles, for example, over a period of eight cardiac cycles. The instantaneous calculating period of the system, i.e. the basic 30 Hz rate, is synchronized with the start of a cardiac cycle, as described above, whereby velocity profile data sets accumulated from cardiac cycle to cardiac cycle correspond to same instants in each cycle. This synchronization is accomplished by determining the above-described threshold crossing to within ±1/16 of the calculation period of the system. The difference between this interpolated threshold crossing and the previous actual data sampling time is added to the normal data sample interval time for one period at each synchronization point. This shifts the subsequent data set sample time to be within ±1/16 of a sample period of exact correspondence with the initial sample point of the preceeding cardiac cycle. With this synchronization, velocity profiles are obtained from the same relative position in several cardiac cycles which allows for meaningful averaging of the profiles. The resulting averaged profile data points exhibit lower variance and, therefore, represent a more accurate measurement of actual blood velocity in the vessel under observation.

For use in velocity profile averaging, the display computer 54A includes a large 16 word×60 word memory array of accumulators 54E. The 16 word dimension accommodates velocity values 10-1 through 10-16 obtained from the sixteen Doppler measuring points. Starting at a cardiac synchronization point, the sixteen word Doppler velocity profile data sets are entered into successive accumulators in the 60 word dimension of the array starting at the first of the 60 word accumulator dimension. At the start of the next cardiac cycle, the memory address returns to the first of the 60 word accumulator dimension. In this way, each new velocity data set is added to the corresponding data from previous cycles. As mentioned above, velocity profile data sets are accumulated over a period of eight cardiac cycles. It here will be noted that with a heart beat rate of one beat per second, and a Doppler computational system operating rate of 30 Hz, thirty velocity profile data sets are accumulated each cardiac cycle. Under such conditions, only one-half the total memory array of accumulators is utilized. By use of a 16×60 words memory array, a heart beat rate as low as 1 beat every two seconds is accommodated.

In addition to adding corresponding velocity profiles over a period of eight cardiac cycles, a table is maintained in the memory of computer 54A of the number of data sets added at each interval along the cardiac cycle. From this table the correct normalization factor for the accumulated values is determined. Since velocity profiles over eight cardiac cycles are averaged, substantially all of the accumulated values are divided by a factor of eight. This table, however, is necessary since the normal cycle-to-cycle variation of the cardiac period may cause the velocity profile accumulators employed near the end of each cycle to contain fewer data sets than the number of cardiac cycles averaged. The velocity profile values accumulated over eight cardiac cycles are divided by the appropriate normalization factor, and the resulting average velocity profile values are transferred through graphics memory 162-1 (FIG. 8) to provide for display 98, shown in FIG. 2C.

Also, instantaneous volume flow calculations are performed by the computational computer 116, in the manner described above, and the results of such computations are supplied to the digital display subsystem 54 for display as waveform 100, shown in FIG. 2C. During averaging of the velocity profiles over eight cardiac cycles, a scrolling display of the calculated instantaneous volume flow values is provided. When the averaged velocity profiles have been calculated, instantaneous volume flow computations are terminated, as is scrolling of instantaneous volume flow display 100. Now, a signal for the pointer 104 is generated by digital display subsystem 54, which pointer is movable along the display 100 to indicate the point in the cardiac cycle at which values for the average velocity profile display 98 are obtained. The pointer is movable over a distance representative of one cardiac cycle, between adjacent cardiac synchronization points obtained from instantaneous volume flow values. A checking routine in the digital display subsystem 54 uses the number of data sets in the cardiac cycle to provide wrap around of the pointer position when stepping either to the right or left under control of switch 106.

In the Doppler Profile With Volume Flow and Cardiac Average operating modes, the B-scan transducer 20 is locked in position at the center of the scan where the B-scan and Doppler axes 34 and 38 intersect. The B-scan transmitter/receiver unit then operates to supply a line of information to the digital display unit 54 at a rate of 10 lines per second. As noted above, in the Doppler Profile with Volume Flow mode, a real-time display 84 of a portion of this line of video data is provided. In the Cardiac Average mode (FIG. 2C) a portion 96 of the last-acquired A-scan line is displayed. The numeric display 102 indicates average volume flow, averaged over the eight cardiac cycles used to obtain the average velocity profile data. The computational computer 116 performs the necessary averaging, and the data is stored by the digital display subsystem for display at display unit 56. Again, because of averaging, this value 102 shows higher accuracy and lower variance than the single cardiac cycle volume flow values 94.

DIGITAL DISPLAY SUBSYSTEM

Details of the Digital Display Subsystem 54 are shown in FIG. 8 to which figure reference now is made. As noted above, Doppler velocity and range data together with volume flow data are supplied to the digital display computer 54A of Digital Display Subsystem 54 from the computational computer 116. Also, data from display mode 74, profile time 106 and neg.-pos.-display 90 controls is supplied to the computer 54A. These are generated as "digital" on or off signals which are directly accommodated by the computer 54A. From the above-mentioned data, and A-scan data, the displays of FIGS. 2B and 2C are synthesized, depending upon the selected Doppler display mode.

The computer 54A shown in FIG. 8, which may comprise an 8085 microcomputer, provides overall display subsystem control, including interpolation between Doppler velocity profile points. Memory associated with the display computer includes a random access memory (RAM) section 54B of working memory, a character generator read only memory (ROM) 54C, a program ROM 54D and the above-mentioned 16×60 words accumulator 54E. Data for display of Doppler velocity profile points, including interpolated velocity profile points, the scales 89 and 93, and necessary annotation (here "CM/SEC", "CC/SEC" and "CC/MIN") is transferred from the display computer 54A to a graphics memory 162-1. The character generator ROM 54C, under control of program ROM 54D is used to generate the annotation and numeric displays 94 and 102. As noted above, accumulator array 54E is used for velocity profile averaging.

Another memory, identified as scrolling memory 162-2, is used for storage of data for the instantaneous volume flow displays 92 and 100 of FIGS. 2B and 2C. Preferably, memory 162-2 comprises a ring buffer which greatly facilitates display of the scrolling instantaneous volume flow display 92. A 256×6 bit ring buffer 162-2 is shown. For the scrolling display, new instantaneous volume flow data is written into the next storage location of the ring buffer. The starting address for reading out the information from the ring buffer is essentially, incremented one location each display to effectively move the display 92 to the left. With this arrangement there is no need to rewrite the entire memory after each display of the scrolling instantaneous volume flow data contained in memory. Instead, as noted above, the address for writing into memory, and the output starting address for reading from the memory simply are, essentially, incremented when new values are written into memory and data for the display is read from memory, respectively.

A third memory, identified as A-scan memory 162-3, is used for the storage of data for the A-scan displays 84. During operation in the B-scan image with cursor operating mode, illustrated in FIG. 2A, one field (one-half frame) of B-scan information is produced and displayed upon travel of the B-scan transducer 20 from one end of the line of travel to the opposite end thereof. The composite B-scan video from the B-scan receiver of the B-scan unit 48 comprises a standard National Technical Systems Committee (United States) signal. For the A-scan display included in FIG. 2A, one line of information per field is acquired and stored at the A-scan memory 162-3. For A-scan storage, a 1024×6 bit memory is employed. Information for A-scan display is obtained from the B-scan receiver output by means of a 6-bit data acquisition system 164 which is operated at a 10 MHz sample rate, whereby 550 samples are obtained and stored.

Television line number and pixel number information for synchronizing reading data from the memories 162-1, 2 and 3 with the NTSC television signal from the B-scan receiver is provided by means of a phase lock loop (PLL) circuit 180 to which the composite video signal from the B-scan receiver is supplied. Clock signals at the horizontal and vertical synchronization rates of the composite video signal are obtained from the phase lock loop 180 and supplied to a television output synchronization circuit 182. Higher frequency pixel clock signals also are obtained from the phase lock loop circuit, which signals also are supplied to the circuit 182. From the horizontal, vertical and pixel information supplied thereto the circuit 182 provides a television line number signal at one output, and a pixel number signal at a second output, which signals provide addresses to the memories 162-1, 2 and 3 for reading therefrom in proper time with scanning of the raster scan video display screen of the visual display means 56. A television synchronization and scanning circuit 184 also responsive to the composite video signal from the B-scan receiver 48 provides the necessary synchronizing signals to a video switch unit 185 to allow video synchronization pulses from the B-scan receiver unit to pass to display unit 56. Video switch 185 is also controlled by the mode setting 74 via computer 54A so that B-scan data is passed when in the B-scan modes, and B-scan data is suppressed when in the Doppler modes.

Outputs from memory means 162-1, 2 and 3 are supplied at the U.S. Standard raster scan television rate, under control of synchronization circuit 182, to a video summer circuit 186 (to which circuit B-scan video also is supplied for B-scan display when in one of the B-scan operating modes). It will be noted that data from the scrolling memory means 162-2 and A-scan memory means 162-3 is connected to the video summer circuit 186 through an interpolation circuit 188. Circuit 188 functions to calculate values between successive data values supplied thereto from the memory means 162-2 and 162-3 and to transmit such interpolated values to the video summer together with the actual data values. Each video line output from the circuit 188 thereby includes at least a minimum number of points required for a display of more pleasing appearance. For data from the scrolling memory, three interpolated points are calculated between each data point, which three points are transmitted to the video summer between adjacent video points.

For display of data from the A-scan memory, different numbers of interpolated points are provided as determined by the span setting and mode setting. For the B-scan image with cursor operating mode wherein the entire A-scan line is displayed, data for the display passes through the interpolation circuit without the addition of interpolated points. However, when less than a full line of A-scan is displayed, in either of the Doppler operating modes, interpolated points are added between A-scan data points. The span control signal is shown supplied to the interpolation circuit for control of the interpolation calculations in accordance with the span setting. A variable number of interpolation points are provided, depending upon the setting of span control means 88; the shorter the span, the greater the number of interpolation points required.

To read different portions of the A-scan line data from the A-scan memory, as required for different span settings, a variable frequency clock 190 is provided, the frequency of which is under control of an output from the digital display computer 54A. The span control signal from the computational computer to the display computer is used to control the frequency of the clock 190. The starting address from which A-scan data is read from memory 162-3 is under control of another signal from the display computer 54A. The depth control signal from the computational computer to the display computer is used to control the memory address for the start of the A-scan display whereby the desired segment of the A-scan line is displayed.

OPERATION

Although the operation of the system is believed to be apparent from the above description, a brief description of the operation now will be provided. With the mode selector switch 74 (FIG. 3) in the illustrated B-scan Image Only position, the pulsed B-scan transmitter/receiver unit 48 (FIG. 1) operates to provide a real-time image at the face of display unit 56; the B-scan video data for this display being supplied to the display unit 56 through the video switch 185 and video summer 186 under control of TV-sync and scanning circuit 184 (FIG. 8).

When a vessel, say a carotid artery, is located within which vessel a quantitive measurement of volumetric blood flow is desired, the selector control 74 (FIG. 3) is switched to the B-scan Image With Cursor position to provide for a visual display such as illustrated in FIG. 2A. In this operating mode the real-time B-scan image is displayed, together with an A-scan display 84 and a cursor 80. Information for the A-scan display is derived from the center scan line of frames of B-scan. B-scan video is supplied to the 6-Bit Data Acquisition system 164 (FIG. 8) where the center line thereof is digitized by a high speed analog-to-digital converter included therein operating at a ten megacycle sampling rate. A-scan lines are stored in the A-scan memory 162-3 from which they are transferred to the display unit 56 through Video Summer 186 for simultaneous display with the cursor 80 and B-scan image.

The cursor 80 (FIG. 2A) is displayed at the center line of the B-scan image, midway between opposite ends of the B-scan. The cursor starting depth and length, or span, are determined by the settings of depth and span control means 86 and 88, respectively, at the front panel 72 of the system. (FIG. 3) Depth and span control signals from control means 86 and 88 are supplied to the computational computer 116 (FIG. 1) through multiplexer 110 and analog-to-digital converter 114 where Doppler cursor signals are calculated in response to depth and span control settings. The calculated Doppler cursor signals are supplied over line 170 (FIG. 1) to the digital display subsystem and stored in the graphic memory 162-1 (FIG. 8) for display under control of display computer 54A. Signals for display of calibrated tick marks 82 (FIG. 2A) also are produced by the digital display subsystem computer 54A for this operating mode.

While in the B-scan Image with Cursor operating mode, the head 24 (FIG. 1) containing the B-scan and Doppler transducers 20 and 22, respectively, is positioned such that the B-scan image plane 36 is substantially normal to the vessel axis 44 as determined by visual observation of the B-scan image 76 (FIG. 2A) of the vessel and maximization of the amplitude of vessel wall reflections 84B and 84C as determined by the A-scan display 84. Additionally, the head 24 is positioned such that the center scan line of the B-scan display, at which the cursor 80 is located, extends diametrically through the vessel. The depth and span controls 86 and 88 (FIG. 3) then are adjusted to positions wherein the cursor 80 spans the image 76 of the vessel. This preliminary positioning of the head 24 accurately establishes the position of the Doppler transducer axis 38 relative to the vessel 42 such that a known angle $\beta$ is established between the Doppler transducer beam axis and vessel axes. Quantitative Doppler velocity measurements from blood flowing in the vessel 42 now are possible.

With the head 24 maintained in proper position while operating in the B-scan Image with Cursor operating mode, operation is switched by control 74 (FIG. 3) to the Doppler Profile with Volume Flow operating mode to provide for the display illustrated in FIG. 2B. In this operating mode the Doppler transmitter/receiver unit 60, under control of timing and control unit 64, operates at a basic 10 Khz rate. Analog Doppler circuitry of standard practice type detects 16 values of velocity at 16 range positions. These values from the 16 Doppler analog channels of the Doppler receiver 68 are sampled and stored in the 16 sample and hold circuits included in the receiver. The 16 velocity signal values are proportional to tissue velocity at measurement points 38-1 through 38-16 along the Doppler transducer axis 38, in the direction of the vessel axis 44. The depth and span of the measurement points is established by the settings of depth and span controls 86 and 88 to thereby correspond with the depth and span of cursor 80. The 16 analog velocity signals are sampled and transferred 30 times a second to the computational computer 116 through multiplexer 110 and and analog-to-digital converter 114. The digitized velocity signals provide a quantitative measure of tissue velocity in the axial direction of the vessel 42 at the measuring points 38-1 through 38-16. From the computational computer 116, the velocity signals are passed to digital display subsystem 54, and then to the display unit 56 to provide for the real-time Doppler velocity profile 87. Signals for the display of calibrated scale 89 are generated by the digital display subsystem 54 to provide the operator with quantitative velocity information of the blood flow.

The computational computer 116 also calculates an instantaneous volume flow value from each velocity data set and with knowledge of the spacing between measurement points. Volume flow calculations involve calculating the velocity profile mid-point from 50% velocity levels. (See FIG. 5.) Half annular areas centered at the calculated velocity profile mid-point are determined, and instantaneous volume flow through each area is obtained as the product of the area and a corresponding velocity value of the velocity data set. (See FIG. 6.) Instantaneous volume flow through the vessel is obtained by summing the calculated instantaneous flow volume values for the individual half annular areas. The resulting summation of velocity and half annuli area products is supplied to the digital display subsystem 54, scaled, and displayed as one point of the scrolling display 92. The scale factor, and scale 93, are a function of the span control 88 setting to allow both large and small flow rates to be observable on the scrolling display 92.

For the numeric display 94 of the volume flow over a cardiac cycle, the cardiac period is determined by the computational computer 116 from the instantaneous flow values. A variable threshold at ¾ of the difference between the maximum and minimum instantaneous flow value is used to identify the start of successive cardiac cycles. The volume flow over a cardiac cycle is simply calculated by accumulating the instantaneous volume flow values over the cardiac cycle, including the fractional value when synchronization occurs, and then dividing by the number, including fraction, of data sets in the cycle.

The timing and control unit 64 includes a programmable timer which provides the timing for the basic 30 Hz Doppler calculation system operating rate. An end of period signal from said timer causes the 16 sample-and-holds at the output from the 16 Doppler analog channels of Doppler receiver 68 to store new velocity values. The same timing signal reactivates the computers in the computational and digital display subsystems 70 and 54, respectively, from their halt states, whereupon the digital display subsystem 54 updates the TV screen of display unit 56 with velocity and volume flow information from the previous data set, and the computational subsystem 70 acquires a new set of data from the 16 Doppler channels of Doppler receiver 68 and computes a new instantaneous volume flow value. The computational computer 116 also checks for the end of a cardiac cycle and, if the end is detected, a new volume flow over the cardiac cycle number is computed. The front panel gain, depth and span controls are sampled and checked for changes from previous settings. Finally, all of the newly acquired and calculated data is passed to the Digital Display subsystem 54 by way of a direct memory access interface, and the computational and digital display computers return to a halt state in preparation for the next timing signal.

With mode selector switch 74 set to the Cardiac Average position, the display illustrated in FIG. 2C is provided. In this operating mode, velocity values are collected and instantaneous volume flow calculations are performed in the manner described above with reference to the Doppler Profile With Volume Flow operating mode. Now, however, individual velocity profiles are averaged over a plurality of cardiac cycles, and a plurality of such average velocity profiles obtained from different points in the cardiac cycle are stored in a memory array of accumulators 54E included in display subsystem 54. (See FIG. 8.) Additionally, instantaneous volume flow values calculated over a two second period are stored in memory 162-2 of Digital display subsystem 54. A small carot, or marker, 104 (FIG. 2C) under the stationary instantaneous volume flow display 100 indicates the temporal position in the cardiac cycle corresponding to the current Doppler velocity profile display 98. Movement of the marker 104 is under control of Profile Time Switch 106 (FIG. 3) at the front panel 72 whereby the operator may select any one of the calculated average velocity profiles for display.

The invention having been described in detail in accordance with requirements of the Patent Statutes, various changes and modifications will suggest themselves to those skilled in the art. As noted above, specific operating values contained in the description are for purposes of illustration only and not by way of limitation. Obviously, the invention is not limited to Doppler computation operation at a basic rate of 30 Hz, or Doppler system repetition frequency of 10 Khz. The number of Doppler velocity signals in a data set is not limited to 16, and velocity and volume flow scales for the displays are not limited to those shown and described above. Also, in the Doppler Profile with Volume Flow operating mode illustrated in FIG. 2B, "real-time" A-scan 84, Doppler velocity profile 87, and volume flow 92 displays are provided. It will be apparent, however, that the system output may be supplied to video signal storage means, such as video tape, or may be connected through a scan converter, or the like, before display of the signals. The use of the term real-time herein is not intended to preclude such arrangements and operations. In addition, other means for obtaining cardiac synchronization signals may be employed in place of the novel cardiac cycle calculation method described above. It is intended that the above and other such changes and modifications shall fall within the spirit and scope of the invention defined in the appended claims.

We claim:

1. In an ultrasonic system for real-time acquisition and scrolling display of instantaneous volume flow data, said system comprising,
    pulse-echo means including transducer means for recurrently beaming pulses of ultrasonic waves across a vessel through which liquid flows and providing a plurality of Doppler velocity signals proportional to liquid flow through the vessel at a plurality of spaced points along a line extending substantially diametrically across the vessel, visual display means, means responsive to said velocity signals and spacing of points along which said signals are obtained for calculating instantaneous volume flow data, means for communicating said instantaneous volume flow data to said visual display means and providing a scrolling visual display of said data thereat, means for scaling said instantaneous volume flow data, a source of calibrated scale data, means including said communicating means for communicating calibrated scale data from said source to said visual display means to provide a quantitative scrolling visual display of instantaneous volume flow thereat, and operator controlled span control means for controlling the spacing between the points along the line at which the velocity signals are obtained, said source of calibrated scale data including volume flow scale data for different scales, said means for scaling said instantaneous volume flow data and the calibrated scale data from said source selected for display also being controlled by the setting of the operator controlled span control means.

2. In an ultrasonic system for real-time acquisition and scrolling display of instantaneous volume flow data, said system comprising, pulse-echo means including transducer means for recurrently beaming pulses of ultrasonic waves across a vessel through which liquid flows and providing a plurality of analog Doppler velocity signals proportional to liquid flow through the vessel at a plurality of points along a line extending substantially diametrically across the vessel, means for digitizing said analog Doppler velocity signals, digital computational computer means responsive to said digitized velocity signals and digital data representative of the spacing between points along which said signals are obtained for calculating instantaneous volume flow data, digital display computer means responsive to instantaneous volume flow data from said computational computer means for scaling said instantaneous volume flow data, first memory means for temporary storage of instantaneous volume flow data from said display computer means, second memory means for storage of data for a plurality of calibrated volume flow scales, cathode ray tube type visual display means, means for communicating instantaneous volume flow and associated calibrated volume flow scale data to said visual display means from said first and second memory means, respectively, and producing a quantitative scrolling visual display of instantaneous volume flow at said visual display means.

3. In an ultrasonic system as defined in claim 2 wherein said visual display means comprises a raster scan video display screen, and said communicating means includes television scanning and synchronizing means.

4. In a method of measuring volume flow of blood through a generally cylindrical-shaped portion of a vessel of a subject from measurements of fluid velocity at spaced points along a line extending substantially diametrically across said vessel, steps comprising, identifying at least one semi-annular area for each measurement point, multiplying the velocity measurements by associated semi-annular areas to obtain instantaneous volume flow values for each area, obtaining a plurality of recurrent velocity measurements each cardiac cycle of the subject, recurrently repeating the identifying, multiplying and summing steps for each of the velocity measurements to obtain a plurality of total instantaneous volume flow values, identifying successive cardiac cycles using said recurrent total instantaneous volume flow values, and summing instantaneous volume flow values obtained over a cardiac cycle to recurrently obtain values of volume flow per cardiac cycle.

5. In a method of measuring volume flow of fluid through a generally cylindrical-shaped portion of a vessel from measurements of fluid velocity at spaced points along a line extending substantially diametrically across said vessel, steps comprising, identifying at least one semi-annular area for each measurement point, multiplying the velocity measurements by associated semi-annular areas to obtain instantaneous volume flow values for each area, and summing the instantaneous volume flow values to obtain a value of total instantaneous volume flow through the vessel, said step of identifying at least one semi-annular area for each measurement point including, using said velocity measurements, calculating a center of flow point along said line, said semi-annular areas being centered at said calculated center of flow point.

6. In a method as defined in claim 5 wherein the step of calculating the center of flow point includes, calculating a fluid velocity value equal to substantially fifty percent of the maximum velocity measurement, identifying two position points along said line at which velocity values are substantially equal to said fifty percent of maximum velocity measurement, the center of flow point comprising substantially the mean position of said two position points.

7. In a method of measuring volume flow of blood through a vessel, the steps including, beaming ultrasonic pulse energy through the vessel at a predetermined angle relative to the vessel axis, receiving reflected ultrasonic energy from the beam and generating a signal, processing said signal to obtain a velocity profile comprising a plurality of signals which are proportional to velocity at a plurality of evenly spaced points along a line extending substantially diametrically across the vessel, calculating a flow midpoint along said line using said velocity profile, multiplying each signal of the velocity profile by an associated area value to obtain a plurality of instantaneous volume flow values, areas of semi-annular shape being employed in the multiplication step, said semi-annular shaped areas being centered at said calculated flow midpoint, and adding the instantaneous volume flow values to obtain a value of total instantaneous volume flow through the vessel.

8. In an ultrasonic system for real-time acquisition of velocity data, said system comprising
pulse-echo means including transducer means for recurrent ultrasonic pulse insonification of an object under examination and providing a plurality of Doppler velocity signals proportional to tissue velocity at a plurality of spaced points over a span of depths within the object,
means for controlling the depth at which the span begins, and
means for controlling the gain of said pulse-echo means for increased gain with an increase in the depth control setting and decreased gain with a decrease in the depth control setting.

9. In an ultrasonic system as defined in claim 8 wherein said pulse-echo means includes pulse transmitter means the gain of which is controlled by said depth control means.

10. In an ultrasonic system as defined claim 9 wherein the pulse-echo means includes pulse receiver means the gain of which also is controlled by said depth control means.

11. In an ultrasonic system as defined in claim 8 wherein the pulse-echo means includes pulse receiver means the gain of which is controlled by said depth control means.

12. In an ultrasonic system for the examination of the interior of objects, such as body parts, the combination comprising,
means for insonification of an object under examination with an ultrasonic wave signal,
means for receiving echo signals from discontinuities over a span of depths within the insonified object and for converting the same to electrical signals,
adjustable means for controlling the depth at which the span for receiving echo signals begins,
means under control of the setting of said adjustable means for controlling the gain of at least one of said insonification means and receiving means to provide for greater gain at greater depth settings and less gain at decreased depth settings.

13. In an ultrasonic system as defined in claim 12 wherein said depth controlling means is under operator control.

14. In an ultrasonic system as defined in claim 12 wherein the gain of both the insonification means and receiver means is controlled by the setting of the depth control means.

15. In a real-time ultrasonic imaging system having first and second operating modes under operator control, said system comprising,
a pulsed real-time B-scan imaging system for periodically providing video field signals comprising recurrent video line signals,
pulse echo means including transducer means for recurrently beaming pulses of ultrasonic waves across a vessel through which liquid flows and providing a plurality of Doppler velocity signals proportional to liquid flow through the vessel at a plurality of spaced points along a line substantially diametrically across the vessel,
A-scan line acquisition means responsive to signals from said B-scan imaging system for acquiring data for display of an A-scan substantially from along said line extending substantially diametrically across said vessel,
means for generating cursor data for identifying the line along which Doppler velocity signals are obtained,
visual display means of the cathode ray tube type,
means for communicating B-scan video signals from said B-scan imaging system, cursor data from said cursor data generating means, and A-scan data from said A-scan acquisition means to said visual display means in the first operating mode of the system for simultaneous display at said visual display means of a real time B-scan image, a cursor, and an A-scan line, and
means for communicating Doppler velocity signals from said pulse echo means to said visual display means in the second operating mode of the system.

16. In a real-time ultrasonic imaging system as defined in claim 15, wherein a Doppler velocity profile is displayed at the visual display means in the second operating mode in response to the Doppler velocity signals, the system including,
means for generating velocity scale signals,
means for communicating velocity scale signals from said means for generating velocity scale signals to said visual display means in the second operating mode of the system for simultaneous display at said visual display means of a velocity scale in association with the Doppler velocity profile provided by said Doppler velocity signals.

17. In a real-time ultrasonic imaging system as defined in claim 16 including,
means for communicating A-scan data from said A-scan acquisition means to said visual display means in the second operating mode of the system for visual display at said visual display means of an A-scan line together with said real-time Doppler velocity profile and associated velocity scale.

18. In a method of calculating the center of flow point of a generally cylindrical-shaped portion of a vessel from measurements of fluid velocity at spaced points along a line extending substantially diametrically across said vessel, said measurements defining a flow profile of arbitrary shape including non-symmetric shapes, the steps comprising,
calculating a fluid velocity value equal to substantially fifty percent of the maximum velocity measurement, and
identifying two position points along said line at which velocity values are substantially equal to said fifty percent of maximum velocity measurement, the center of flow point comprising substantially the mean position of said two position points.

19. In a method as defined in claim 18 wherein the fluid comprises blood flowing through a vessel of a subject, and
the measurements of fluid velocity are obtained by use of a pulsed ultrasonic Doppler system.

20. An ultrasonic system for acquisition and display of volume flow data, said system comprising
pulse-echo means includng transducer means for recurrently beaming pulses of ultrasonic waves across a vessel through which liquid flows and providing a plurality of Doppler velocity signals proportional to liquid flow through the vessel at a plurality of spaced points along a line extending across the vessel, operator controlled span control means for controlling the spacing between the points along the line at which the velocity signals are obtained, means responsive to said velocity signals and spacing of points along which said signals are obtained for calculating volume flow data, means for scaling said volume flow data, a source of calibrated volume flow scale data including volume flow scale data for different scales, visual display means, means for communicating said volume flow data and volume flow scale data to said visual display means for providing a quantitative volume flow display thereat, said means for scaling said volume flow data and the calibrated scale data from said source selected for display being controlled by the setting of the operator controlled span control means.

21. In a method of producing cardiac synchronization signals from recurrent measurements of instantaneous volume flow of blood through a vessel, steps comprising from instantaneous volume flow measurements, identifying values of maximum and minimum volume flow during a cardiac cycle, using the difference between the maximum and minimum volume flow values, identifying a threshold volume flow equal to a value intermediate said maximum and minimum volume flow values, determining when the volume flow during the next cardiac cycle equals the threshold volume flow and producing a cardiac synchronization signal in response thereto.

22. In a method as defined in claim 21 including repeating the steps of claim 21 each cardiac cycle for producing a new threshold volume flow value each cardiac cycle.

* * * * *